(12) United States Patent
Nolan

(10) Patent No.: US 6,273,092 B1
(45) Date of Patent: Aug. 14, 2001

(54) METHODS FOR TREATING VARIOUS EYE DISORDERS

(76) Inventor: Gerard M. Nolan, 565 Waterville Rd., Avon, CT (US) 06001

( * ) Notice: Subject to any disclaimer, the term of this patent is extended or adjusted under 35 U.S.C. 154(b) by 0 days.

(21) Appl. No.: 09/667,270

(22) Filed: Sep. 22, 2000

(51) Int. Cl.⁷ ................................................. A61B 19/00

(52) U.S. Cl. ............................................................. 128/898

(58) Field of Search .................................... 351/202, 246; 424/78.04, 427, 428; 514/912, 913, 914, 915; 128/898

(56) References Cited

U.S. PATENT DOCUMENTS 5,778,893 * 7/1998 Potter ................................... 128/898

\* cited by examiner

*Primary Examiner*—George Manuel
(74) *Attorney, Agent, or Firm*—Reed Smith LLP; William J. McNichol; Nanda P. B. A. Kumar

(57) ABSTRACT

The present invention is directed to methods for restoring reading vision and increasing the amplitude of accommodation in presbyopic patients. The method involves topically administering to the patient an amount of a composition sufficient to inhibit acetylcholine esterase activity in the eye of the patient. The invention discloses dose ranges of acetylcholine esterase inhibitor in the composition used for restoring reading vision and increasing the amplitude of accommodation in presbyopic patients and successful correction of presbyopia in these patients. The methods disclosed herein are also used to treat other disorders such as dry eye syndrome, hyperopia, myopia, amblyopia, glaucoma and cataracts.

38 Claims, 2 Drawing Sheets

| | Day 0 | Day 1 | Day 2 | Day 3 | Day 4 | Day 5 | Day 6 | Day 7 |
|---|---|---|---|---|---|---|---|---|
| 20/200 | | | | | | | | |
| J 16 | | | | | | | | |
| 20/100 | | | | | | | | |
| J 10 | X | | | | | | | |
| 20/70 | | | | | | | | |
| J 7 | | | | | | | | |
| 20/50 | | | | | | | | |
| J 5 | | | | | | | | |
| 20/40 | | | | | | | | |
| J 3 | | | | | | | | |
| 20/30 | | | | | | | | |
| J 2 | | | | | | | X | X |
| 20/25 | | X | X | X | X | X | | |
| J 1 | | | | | | | | |
| 20/20 | | | | | | | | |
| J +1 | | | | | | | | |

FIG. 1

METHODS FOR TREATING VARIOUS EYE DISORDERS

FIELD OF THE INVENTION

The present invention relates to newly identified pharmacological treatment to correct presbyopia. Specifically, the invention provides methods for restoring reading vision and increasing amplitude of accommodation by topical administration of acetylcholine esterase inhibitors to the eyes of presbyopic patients.

BACKGROUND OF THE INVENTION

The image of an infinitely distant object will fall in front of the retina in myopia (nearsightedness), on the retina in emmetropia (normal sightedness), and behind the retina in hyperopia (farsightedness), when these eyes are exerting zero accommodation. The emmetropic eye forms sharp retinal imagers of distant objects with the lens of the eye in relaxed accommodation. This ideal optical human condition of emmetropia is possible as a result of a function of corneal curvature and axial length of the eye and takes into account that parallel rays of light travelling from air will bend when passing through the cornea surface and into the liquid environment of the eye. Normally, the emmetrope can see distant scenes sharply and, in addition, can see objects held close to the eye without awareness of any focusing by the eye. The process of focusing upon a near object, called accommodation, is accomplished by the muscles of the ciliary body of the eye contracting to vary the shape of the crystalline lens of the eye. To see at a distance, the ciliary muscles are relaxed; to see nearby, the ciliary body contracts to reshape the lens. The amount of accommodation exerted from the relaxed state of the muscles of the ciliary body to the contracted state of the ciliary muscles (i.e., to full accommodation) of the eye is termed the amplitude of accommodation. When the eye is fully accommodated, the point in space which is focused upon the retina is called the near point of the eye, or the nearest point of distinct vision.

Accommodation is measured in diopters. A diopter is defined as 1/the distance in meters to the near point of vision. In both emmetropic individuals and myopic individuals, who have been treated by corneal surgery, the ability to accommodate is gradually lost with age. In fact, the ability to reshape the lens to focus upon a near point may be completely lost after age 40 years. This decrease in the amplitude of accommodation and the consequent loss of near vision is called presbyopia and is thought to be a normal part of the aging process. The inverse relationship between age and the amplitude of accommodation can be seen in Table 1.

TABLE 1

Relationship Between Age, Amplitude of Accommodation and Near Vision for Emmetrope

| Age | Amplitude of Accommodation (Diopters) | Near Point For Emmetrope (cm) |
|---|---|---|
| 10 | 14.0 | 7.0 |
| 20 | 10.0 | 10.0 |
| 30 | 7.0 | 14.2 |
| 40 | 4.5 | 22.2 |
| 45 | 3.5 | 28.5 |
| 50 | 2.5 | 40.0 |
| 55 | 1.75 | 57.0 |
| 60 | 1.00 | 100.0 |
| 65 | 0.50 | 200.0 |
| 70 | 0.25 | 400.00 |

Physiologically, accommodation is under the influence of the parasympathetic nervous system and occurs through the chemical action of acetycholine on muscle fibers of the ciliary body. Contraction of the ciliary body muscles decreases the tension of the lens ligaments, which allows the lens to focus at near point.

Acetylcholine, when working on the eye or other smooth muscles of the body is regulated by the natural cholinesterase enzyme which breaks down acetylcholine and thus turns off its parasympathetic effect on muscles. In an effort to correct presbyopia, the effect of acetylcholine on the muscles of the eye could be increased either by adding an acetylcholine like drug such as pilocarpine, or by blocking the breakdown of acetylcholine with a drug which inhibits the natural cholinesterase (e.g., a cholinesterase inhibitor).

There have been problems with the first approach: When pilocarpine hydrochloride, an acetylcholine like drug, sold as SALAGER® (MGI Pharma, Minnetonka, Minn.), is applied to an emmetropic eye, the increased parasymathetic effect leads to enhanced near vision but at the sacrifice of distant vision. The emmetropic eye becomes myopic as a consequence of this adverse side effect, thus acetylcholine treatment to correct presbyopia has not been effective. Likewise, the second approach, the use of cholinesterase inhibitors, has been unsuccessful because of similar side effects from the cholinesterase drugs used in current concentrations. No other pharmacological agents have been found to restore near vision in an individual with presbyopia. Thus presbyopia is considered untreatable with current pharmacological agents.

SUMMARY OF THE INVENTION

The present invention is based, at least in part, on the discovery of indirectly improving endogenous acetylcholine levels of eye without adverse effects, thereby reversing ciliary muscle dysfunction and presbyopia, by using an acetylycholine esterase inhibitor (AChE inhibitor). Specifically, the present invention provides methods for, among other things, restoring reading vision without sacrificing distant vision and inducing myopia in emmetropics. Therefore, this invention provides several advantages over prior art methods employed for restoring near vision in presbyopic patients. The methods disclosed herein can also be used to treat other disorders such as dry eye syndrome, hyperopia, myopia, amblyopia, glaucoma and cataracts without any adverse side effects.

BRIEF DESCRIPTION OF THE FIGURES

FIG. 1 is a graph that shows mean uncorrected near vision improvement.

DETAILED DESCRIPTION OF THE INVENTION

Figure 2:
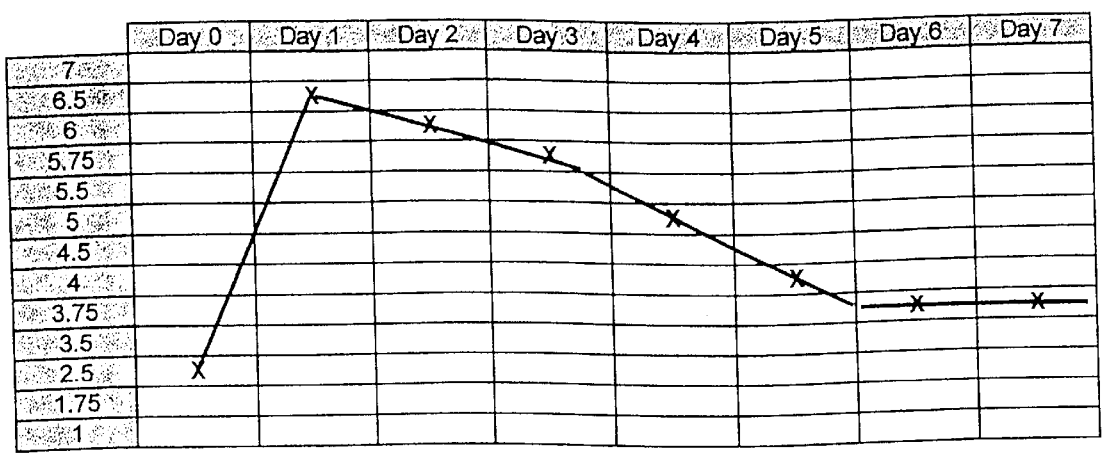
FIG. 2 is a graph that shows mean amplitude of accommodation improvement. On the x-axis are the values of amplitude of accommodation (diopters).

The invention relates to methods for restoring lost reading or near vision and increasing the amplitude of accommodation in presbyopic patients with emmetropic eyes. The method involves the topical application of an acetylcholine esterase (AChE) inhibitor to the patient. The method can improve near vision without any side effect such as blurring, loss of distant vision or induction of myopia. The medication, applied in appropriate concentration, will allow the patient to achieve near vision, without corrective lenses, which will last several days. Moreover, unlike corrective reading glasses, because of the increase in amplitude of accommodation by practicing the present invention, the individual will be able to focus at many different lengths between the near point and the distant vision. This eliminates the need for bending the head in order to bring an object in line with the lenses of the reading glasses. For the emmetrope, the present invention eliminates for several days the need for corrective reading glasses. For the myopic or hyperopic individual, the present invention eliminates the need for bifocal lenses.

Acetylcholine esterase inhibitors are known to one skilled in the art. There are at least two AChE inhibitor drugs currently approved for clinical use on the eye in the United States. They are (2-mercaptoethyl)trimethylammonium iodide O,O-diethyl phosphorothioate sold as PHOSPOHLINE IODIDE® (Wyeth-Ayerst, Philadelphia, Pa.), and physostigmine (also known as eserine) sold as ANTILIRIUM® (Forest Pharmaceuticals, St. Louis, Mo.). PHOSPHOLINE IODIDE is dispensed as eyedrops at a desired potency. PHOSPHOLINE IODIDE of various concentrations, such as for example 0.25%, 0.125%, 0.06% and 0.03% and a pharmaceutically acceptable sterile diluent to dilute the concentrated form of this drug are commercially available. PHOSPHOLINE IODIDE is currently used for glaucoma and accommodative esotropia but there has been no successful use of this drug for presbyopia because of many adverse side effects of the drug especially when used in the standard doses established for glaucoma and accommodative esotropia. As such, PHOSPHOLINE IODIDE is not a preferred drug even to treat glaucoma and accommodative esotropia because of many adverse side effects caused by this drug when it is used in the current regimen of multiple times a day at high concentrations. Some of the side effects known to be caused by the currently recommended doses of this drug (for glaucoma at 0.12 and 0.25 BID) are iris cysts, cataract formation especially anterior subcapsular, posterior synechiae and elevated intraocular pressure.

In the new method, the cholinesterase inhibitor, such as phospholine iodide, administered in concentrations many fold more dilute than currently available pharmacological preparations, applied to the eye before sleep will achieve a restoration of the ability to accommodate with none of the unacceptable side effects of the usual pharmacological preparations and without the loss of distance vision. The effect of one administration at night can last for many days and replace the need for corrective reading lenses during that time. The present invention shows that the effective concentration of AChE inhibitor in the composition to treat presbyopia can be very low (for example, as low as at least 0.001% to about 0.0075% of PHOSPHOLINE IODIDE) to be effective. The invention discloses that such a concentration is extremely useful medically. Specifically, this lower dose range is especially useful in providing eye drugs that will contain a concentration of AChE inhibitor that is low enough to be both safe and effective.

The composition administered to the eye should have a pharmaceutically acceptable carrier and a selected AChE inhibitor suspended or dissolved in the carrier. The concentration of AChE inhibitor in the composition administered to the eye and the mothod of administration of the composition in accordance with this invention depends on the type of AChE inhibitor containing composition used for therapy. For example, preferred concentrations of PHOSPHOLINE IODIDE in the PHOSPHOLINE IODIDE containing composition are from about 0.25% to about 0.001%. More preferred PHOSPHOLINE IODIDE concentrations are from about 0.15% to about 0.005%. Most preferred PHOSPHOLINE IODIDE concentrations are 0.12%, 0.03% and 0.0075%. It is preferred to apply PHOSPHOLINE IODIDE topically to the eyes in the form of eyedrops. Although it is preferred that these solutions with various concentrations of PHOSPHOLINE IODIDE are stored in a refrigerator, they an be stored at room temperature for about two months or even beyond two months without losing their efficacy to restore near vision in presbyopic patients.

A solution containing chlorobutanol (0.55%), mannitol (1.2%) boric acid (0.6%) and exsiccated sodium phosphate (0.026%) can be used as a carrier solution and/or as a diluent for PHOSPHOLINE IODIDE. While this solution is presently sold as a diluent in the kit containing PHOSPHOLINE IODIDE, other pharmaceutically acceptable carriers or excipients that are known to enhance membrane permeability and cellular uptake of the drug can be used with or without modification for application to the eye. Such carriers are known to one skilled in the art.

For the method of the invention to be effective, it is believed that the AChE inhibitor should be administered to the eye in such a way that it increases acetylcholine levels in the eye or ciliary muscle sufficient to improve accommodation. In a preferred embodiment of the invention, the AChE inhibitor is administered at bedtime. A single topical application of a given AChE inhibitor at bedtime can enhance the strength of the ciliary body muscle and significantly improve the uncorrected near visual acuity in the phakic emmetropic patient for a few days. For example, application of one to two drops of PHOSPHOLINE IODIDE of a selected concentration at bedtime can restore reading vision in presbyopic patients for at least five days. Preferably, the following steps are followed every time AChE inhibitor is applied to the patient. The first step is to read for about 30 minutes. The second step is to administer an AChE inhibitor of a selected concentration. The third step is to sleep. Without wishing to be bound by any theory or explanation, it is believed that the reading for about 30 minutes preconditions eye muscles to respond better to the AChE inhibitor treatments. It takes about 6 to 8 hours of sleep to notice the restoration. If one is awaken in the middle of sleep, the individual may notice partial effect but after 6 to 8 hours of sleep the effect will be maximized. By the term "bedtime" it is meant that the time when the patient goes to sleep for about 6 to 8 hours, regardless of whether it is during the day or night time.

AChE inhibitor can be administered either to the dominant and/or the non-dominant eye. It is known that usually one eye is "dominant" with respect to the other and with both eyes open the image from the dominant eye will be perceived more than the non-dominant eye. To show that the restoration of near vision is the result of the effect of AChE inhibitor and not because of subjectivity of the dominant eye being preferred over the non-dominant eye, one can treat the weaker or non-dominant eye. By treating the weaker or non-dominant eye, one can show that the weaker eye becomes stronger than the dominant eye in every treated patient and that the restoration of near vision by AChE inhibitor is real, not because of the dominant eye. Also by treating only one eye, the patient can see the improvement and can judge when to apply another dose (within 7–10 days after the first dose) as the non-dominant eye reverts toward seeing like the dominant eye. Additionally, this allows to check for any side effects and making comparison to the untreated eye.

It should be noted that the method of this invention can be successfully used to correct presbyopia in patients having emmetropic eyes with a normal crystalline lens. The method can also enhance the near vision of an individual who has the normal crystalline lens, but has no iris. However, the method may not be successful to correct presbyopia in presbyopic patients with artificial and rigid intraocular lenses (IOL's). IOL's are inserted at the time of cataract surgery and in refractive procedures to make an individual emmetropic by clear lens extraction.

Accordingly, by practicing the present invention, the near point of distinct vision and also amplitude of accommodation of emmetropic eye can be increased by a single topical application. The near point of an emmetrope can be calibrated into amplitude of accommodation (by the formula D=1/distance in meters to the near point of vision). Increase in amplitude of accommodation can be measured by techniques well known to those skilled in the art. In other words, a suitable dose of AChE inhibitor administered at bedtime can allow the eye to accumulate sufficient stockpiles of acetylcholine by inhibiting acetylcholine esterase activity in the eye and strengthen the ciliary body leading to the improvement in the near point of distinct vision and amplitude of accommodation for sometime. Most middle age emmetropes with presbyopia have near points at arms length (i.e., they can see the near print only if they move it further and further away from the eye). Reading distance is, generally considered to be 33 cm to 35 cm; arms length is greater than this distance. By practicing the method of the present invention, a middle age patient with 20/70 vision at arms length after treatment with AChE inhibitor can obtain 20/20 vision at 12 inches for over five days. To sustain this 20/20 vision at 12 inches beyond this period, the treatment can be repeated in the same fashion. Moreover, by practicing the method of the invention, the restoration of near vision can be achieved in myopes and hyperopic presbyopes who have their distant emmotropic correction with glasses or contact lenses. It eliminates the need for bifocal glasses.

While the detailed discussion of the treatment methods for restoring reading vision in patients suffering from presbyopia disorder has been provided in the text above, the same methods and the concentrations of AChE inhibitor in the compositions described above can also be used to treat other eye disorders as described in the paragraphs below.

The method of the present invention also provides a method for treatment and prevention of dry eye syndrome. The dry eye problem is due to lack of certain components in human tears and is known to those skilled in the art. In dry eye syndrome the tears evaporate too quickly and the patients need supplements of lubricating drops (artificial tears). There has been described treatment of patients with dry eye syndrome using oral pilocarpine. While there has been recovery from the dry eye syndrome, the oral administration of pilocarpine has not been without side effects. Further, such oral administration implicates the entire body in an effort to secure an effect in the eyes. A treatment using AChE inhibitor decreases the tear breakup time (tears stay on the eye longer) without side effects. This invention can reverse the process of old age dry eye syndrome by reactivating the meibomian glands, which supply the oil components to basic tears.

The method of the present invention further provides a treatment method for hyperopia. As described elsewhere, AChE inhibitor restores reading vision in presbyopic patients and increases the accommodative amplitude. The disease hyperopia (farsightedness), maybe prevented by increasing the amplitude of accommodation in the young hyperopes.

The method of the present invention further provides treatment for myopia. Several myopic presbyopics have also noticed a shift in distance correction towards hyperopia or a reduction of their myopia after AChE inhibitor treatment. Therefore, it is believed that treatment with AChE inhibitor can be a treatment to prevent and reverse the disease myopia.

The method of the present invention further provides treatment for amblyopia. Medical dictionary defines amblyopia as "dimness of vision without detectable organic lesion of the eye". By using AChE inhibitor, patients can notice an increase of image size after treatment. Their non-dominant eye sees better than their dominant eye. Thus, AChE inhibitor treatment can be used in accordance with the present invention in relative or absolute amblyopics to improve inherent weakness by magnifying image.

The method of the present invention further provides treatment for a prevention of glaucoma. It is known that there is an age correlation between the most common variety of glaucoma (open angle glaucoma) and presbyopia. Also, there are glaucoma agents that actively stimulate the ciliary body to achieve pressure reduction in glaucoma. Furthermore, there are theories that in glaucoma, lens proteins disintegrate and/or the ciliary body secretes proteins abnormally (pseudo exfoliation syndrome). By keeping the ciliary body chronically active as in the treatment of presbyopia, we can keep pressures at a normal level without needing shock therapy to the ciliary body as in high doses of glaucoma medicines. By keeping the lens active as in treatment of presbyopia prevents the ciliary body from abnormally secreting and prevents the disintegration of lens proteins.

The method of the present invention still further provides treatment for cataracts. It is known that there is an age correlation of presbyopia and cataract formation. Currently, AChE inhibitor (PHOSPHOLINE IODIDE) is being used to treat glaucoma and accommodative estropia and the anterior sub capsular cataract formation is a side effect of prior art therapeutic doses. However with treatment with the new method for three years, there was no cataract formation in the treated eye versus the non-treated eye. By practicing the method of the present invention, one can keep the lens flexible through accommodation. This will prevent the disintegration of lens proteins (cataract formation). To prevent cataract formation in both eyes, AChE inhibitor should be applied to both eyes. Simply by practicing the methods disclosed herein during the course of last three years, it has been found that, there was no disintegration of lens proteins and cataract formation in the treated eye as opposed to the non-treated eye.

EXAMPLE

The example below is carried out using standard drug administration techniques, that are well known and routine to those of skill in the art, except where otherwise described in detail. The example is illustrative, but does not limit the invention.

Treatment of Emmetropes with Presbyopia

After a comprehensive examination of patients, seven emmetropes with presbyopia were identified for the treatments. The mean age of the patient was 48.5 years. These emmetropic patients were treated with (2-mercaptoethyl) trimethylammonium iodide O,O-diethyl phosphorothioate sold under the trademark PHOSPHOLINE IODIDE. Each time only one drop of one of the three different doses of 0.12%, 0.3% and 0.0075% concentrations were topically applied to the non-dominant eye of each patient. Patients were administered medication to the non-dominant eye at bedtime after reading for 30 minutes. The treatment was repeated at five to seven day intervals.

Shown in FIGS. 1 and 2 are the results of this treatment. FIG. 1 shows mean uncorrected (i.e., without reading glasses) near vision improvement. FIG. 2 shows mean amplitude of accommodation improvement. Pre-treatment uncorrected near vision was 20/50 to 20/70 (see FIG. 1) and mean pre-treatment amplitude of accommodation was 2.5 diopters. Examination of patients on days one to five showed considerable increase in near visual acuity from 20/20 to 20/25 (see FIG. 1). The amplitude of accommodation improved to 2.5 times (see FIG. 2). On the first day after the treatment, patients noticed a slight decrease of light sensitivity in dull illumination. This sensitivity subsided by the following day. There was a sustained accommodative effect from the first five days even though there was some tapering of the effect on day six or seven. Even on day seven, the amplitude of accommodation was significantly greater (1.5 times) than that of day zero. Near vision was restored in this manner without major side effects. Patients noticed that they regained the ability to thread a needle, suffered less computer strain and experienced fewer headaches. Patients could read newspaper print without corrective lenses for near vision.

While this invention has been described with reference to specific embodiments, those of ordinary skill in the art will understand that variations in these methods and compositions may be used and that it is intended that the invention may be practiced otherwise than as specifically described herein. Accordingly, this invention includes all modifications encompassed within the spirit and scope of the invention as defined by the claims.

What is claimed is:

1. A method for restoration of reading vision of a patient which comprises topically administering to one or both eyes of the patient an amount of a composition sufficient to inhibit acetylcholine esterase activity in the eye of the patient.

2. The method of claim 1, wherein the composition is administered at bedtime.

3. The method of claim 2, wherein the composition has (2-mercaptoethyl)trimethylammonium iodide O,O-diethyl phosphorothioate.

4. The method of claim 3, wherein the composition has (2-mercaptoethyl)trimethylammonium iodide O,O-diethyl phosphorothioate content of 0.001% to 0.25%.

5. The method of claim 4, wherein the composition has (2-mercaptoethyl)trimethylammonium iodide O,O-diethyl phosphorothioate content of 0.0075%.

6. The method of claim 4, wherein the composition has (2-mercaptoethyl)trimethylammonium iodide O,O-diethyl phosphorothioate content of 0.03%.

7. The method of claim 4, wherein the composition has (2-mercaptoethyl)trimethylammonium iodide O,O-diethyl phosphorothioate content of 0.12%.

8. The method of claim 1, wherein the composition has a pharmaceutically acceptable buffer solution.

9. The method of claim 1, wherein the eye is a dominant eye or a non-dominant eye.

10. The method of claim 9, wherein the eye is a non-dominant eye.

11. A method of increasing the amplitude of accommodation to correct presbyopia in a presbyopic patient which comprises administering to one or both eyes of the patient an effective amount of acetylcholine esterase inhibitor containing composition to the eye of a patient in need of said therapy.

12. The method of claim 11, wherein the composition is administered at bedtime.

13. The method of claim 12, wherein the acetylcholine esterase inhibitor containing composition has (2-mercaptoethyl)trimethylammonium iodide O,O-diethyl phosphorothioate.

14. The method of claim 13, wherein the composition has (2-mercaptoethyl)trimethylammonium iodide O,O-diethyl phosphorothioate content of 0.001% to 0.25%.

15. The method of claim 14, wherein the composition has (2-mercaptoethyl)trimethylammonium iodide O,O-diethyl phosphorothioate content of 0.0075%.

16. The method of claim 14, wherein the composition has (2-mercaptoethyl)trimethylammonium iodide O,O-diethyl phosphorothioate content of 0.03%.

17. The method of claim 14, wherein the composition has (2-mercaptoethyl)trimethylammonium iodide O,O-diethyl phosphorothioate content of 0.12%.

18. The method of claim 11, wherein the composition has a pharmaceutically acceptable carrier buffer solution.

19. The method of claim 11, wherein the eye is a dominant eye or non-dominant eye.

20. The method of claim 19, wherein the eye is a non-dominant eye.

21. A method for restoration of reading vision of a presbyopic patient which comprises topically administering to one or both eyes of the patient an amount of a composition sufficient to inhibit acetylcholine esterase activity in the eye of the patient, wherein the method does not affect distant vision and does not induce myopia.

22. The method of claim 21, wherein the composition is administered at bedtime.

23. The method of claim 22, wherein the composition has (2-mercaptoethyl)trimethylammonium iodide O,O-diethyl phosphorothioate.

24. The method of claim 23, wherein the composition has (2-mercaptoethyl)trimethylammonium iodide O,O-diethyl phosphorothioate content of 0.001% to 0.25%.

25. The method of claim 24, wherein the composition has (2-mercaptoethyl)trimethylammonium iodide O,O-diethyl phosphorothioate content of 0.0075%.

26. The method of claim 24, wherein the composition has (2-mercaptoethyl)trimethylammonium iodide O,O-diethyl phosphorothioate content of 0.03%.

27. The method of claim 24, wherein the composition has (2-mercaptoethyl)trimethylammonium iodide O,O-diethyl phosphorothioate content of 0.12%.

28. The method of claim 21, wherein the composition has a pharmaceutically acceptable buffer solution.

29. The method of claim 21, wherein the eye is a dominant eye or a non-dominant eye.

30. The method of claim 29, wherein the eye is a non-dominant eye.

31. A method for treating a patient suffering from an eye disorder which comprises topically administering to one or both eyes of the patient an amount of a composition sufficient to inhibit acetylcholine esterase activity in the eye of the patient, wherein the eye disorder is dry eye syndrome, hyperopia, myopia, amblyopia, glaucoma or cataracts.

32. The method of claim 31, wherein the composition is administered at bedtime.

33. The method of claim 32, wherein the composition has (2-mercaptoethyl)trimethylammonium iodide O,O-diethyl phosphorothioate.

34. The method of claim 33, wherein the composition has (2-mercaptoethyl)trimethylammonium iodide O,O-diethyl phosphorothioate content of 0.001% to 0.25%.

35. The method of claim 34, wherein the composition has (2-mercaptoethyl)trimethylammonium iodide O,O-diethyl phosphorothioate content of 0.0075%.

36. The method of claim 34, wherein the composition has (2-mercaptoethyl)trimethylammonium iodide O,O-diethyl phosphorothioate content of 0.03%.

37. The method of claim 34, wherein the composition has (2-mercaptoethyl)trimethylammonium iodide O,O-diethyl phosphorothioate content of 0.12%.

38. The method of claim 31, wherein the composition has a pharmaceutically acceptable carrier buffer solution.

* * * * *